United States Patent
Bellido Cabello De Alba et al.

(10) Patent No.: US 9,416,083 B2
(45) Date of Patent: Aug. 16, 2016

(54) METHOD OF ISOLATING INGENOL

(71) Applicant: INDENA S.P.A., Milan (IT)

(72) Inventors: Maria Luz Bellido Cabello De Alba, Cordoba (ES); Giovanni Appendino, Cordoba (ES); Alberto Pagani, Cordoba (ES); Eduardo Munoz Blanco, Cordoba (ES)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 14/922,581

(22) Filed: Oct. 26, 2015

(65) Prior Publication Data

US 2016/0039733 A1 Feb. 11, 2016

Related U.S. Application Data

(63) Continuation of application No. 14/348,750, filed as application No. PCT/EP2012/069452 on Oct. 2, 2012, now abandoned.

(30) Foreign Application Priority Data

Oct. 4, 2011 (ES) .................................. 201131601

(51) Int. Cl.
| | |
|---|---|
| *C07C 45/85* | (2006.01) |
| *C07C 45/78* | (2006.01) |
| *C07C 45/80* | (2006.01) |
| *C07C 67/60* | (2006.01) |
| *C07C 45/65* | (2006.01) |
| *B01D 15/08* | (2006.01) |
| *C07C 67/08* | (2006.01) |
| *C07D 319/08* | (2006.01) |

(52) U.S. Cl.
CPC ................ *C07C 45/85* (2013.01); *B01D 15/08* (2013.01); *C07C 45/65* (2013.01); *C07C 45/78* (2013.01); *C07C 45/80* (2013.01); *C07C 67/08* (2013.01); *C07C 67/60* (2013.01); *C07D 319/08* (2013.01)

(58) Field of Classification Search
None
See application file for complete search history.

(56) References Cited

PUBLICATIONS

Appendino et al., J. Nat. Prod. 1999, 62, 76-79.*
Bagavathi et al., Chemical Sciences, 46, No. 10. pp. 1426-1433, 1991.*
Appendino, et al., "An Expeditious Procedure for the Isolation of Ingenol from the Seeds of Euphorbia lathyris", J. Nat. Prod. 1999, 62, 76-79.
Bagavathi, et al., "On the Chemistry of Ingenol, IV: Ingenol from Seeds of Euphorbia lathyris L. and Preparation of (9R)[(9S)]-9-Deoxo-9-hydoryingenol with some Corresponding 3- and 9-Esters", Chemical Sciences, 46, No. 10, pp. 1426-1433, 1991.
International Search Report and Written Opinion issued in counterpart PCT Application No. PCT/EP2012/069452 on Jan. 8, 2013.

* cited by examiner

*Primary Examiner* — Karl J Puttlitz
(74) *Attorney, Agent, or Firm* — Silvia Salvadori, P.C.; Silvia Salvadori

(57) ABSTRACT

The present invention relates to a new method for isolating ingenol ($C_{20}H_{28}O_5$) from mixtures of diterpenoid esters and ingenol esters in a single step. Ingenol isolated by means of this method can be used as a precursor for the synthesis of biologically active ingenol derivatives, such as ingenol-3-angelate and ingenol-3-tigliate.

7 Claims, No Drawings

METHOD OF ISOLATING INGENOL

This U.S. non-provisional application is a continuation of U.S. application Ser. No. 14/348,750 filed on Mar. 31, 2014 which is a U.S. National Stage of PCT/EP2012/069452, filed on Oct. 2, 2012, which claims priority to and the benefit of Spanish Application No. P201131601, filed on Oct. 4, 2011, the contents of which are all incorporated herein by reference in their entireties.

FIELD OF THE INVENTION

The present invention pertains the field of biology, pharmacy and medicine. More specifically, the present invention relates to a method of isolating ingenol from mixtures of diterpenoid esters and ingenol esters, more particularly when said mixtures come from plants, specifically from seeds of the *Euphorbia* genus and, more specifically from seeds of the *E. lathyris* species.

STATE OF THE ART

Ingenols are compounds which, even though they can be obtained by chemical synthesis, they are also present fundamentally in plants of the Euphorbiaceae family, especially in those varieties with purgative activity [Evans F J and Kinghorn A D J. Linn. Soc. Bot. (London) 1977; 74:23-35; Evans F J and Taylor S E. In Progress in the Chemistry of Organic Natural Products; Herz W, Grisebach H, Kirby G W, Eds.; Springer: New York, 1983; 44:1-99]. Specifically ingenol ($C_{20}H_{28}O_5$) (CAS registry number 30220-46-3) (Formula 1) has been isolated from the seeds of plants of the *Euphorbia lathyris* L. species, commonly known as spurge. Spurge seed oil is marketed in different countries worldwide and is an important raw material for the chemical industry because it is used in the composition of a number of products such as paints, varnishes, cosmetics, lubricants, plastics, biodiesel, etc.

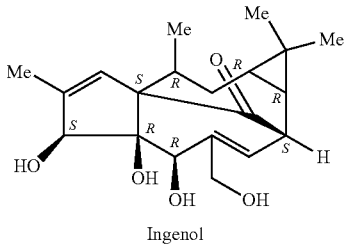

(Formula 1)

Ingenol

Me: $CH_3$ throughout the Present Specification

Enormous interest in the ingenol compound and its derivatives has been raised in recent years due to its important biological activities. Certain ingenols and especially the derivatives esterified at position 3', whether they are natural or obtained by partial synthesis, present potent anticarcinogenic and antiviral activity [Ogbourne S M et al. Cancer Res 2004; 64:2833-9; Benhadji K A et al. Br J Cancer. 2008; 99(11): 1808-15; Kedei N et al. Cancer Res. 2004; 64(9):3243-55; Warrilow D et al., AIDS Res Hum Retroviruses. 2006; 22(9): 854-64; Fujiwara M et al., Antimicrob Agents Chemother. 1996; 40(1):271-3]. Partial synthesis is understood as the isolation of ingenol from plants containing it and the substitution in its molecular structure by suitable chemical reactions in each case of groups leading to the different derivatives of interest. Said derivatives esterified at position 3' which present biological activity and can be used in clinical practice are preferably ingenol-3-tigliate (Formula II) and ingenol-3-angelate (Formula III).

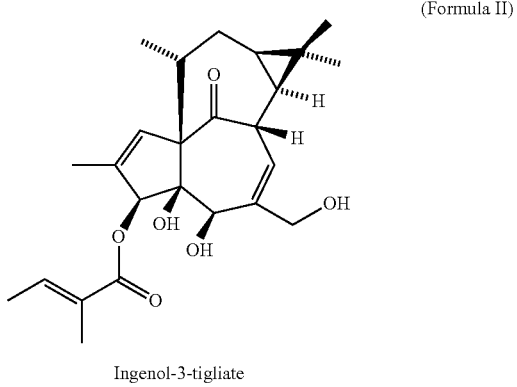

(Formula II)

Ingenol-3-tigliate

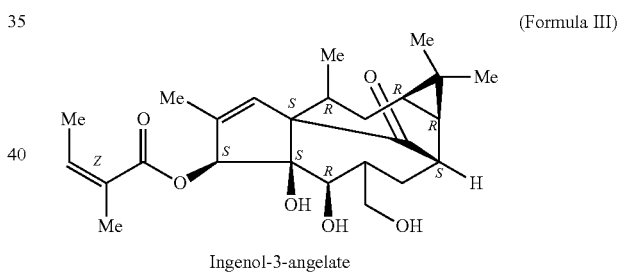

(Formula III)

Ingenol-3-angelate

Ingenol is present in the form of esters in mixtures with diterpenoid esters, in plants and in plant extracts. However, spurge seeds are the only commercial source for isolating ingenol from which it is possible to obtain the biologically active ingenol derivatives used in clinical practice by means of different chemical methods. Said seeds have a complex matrix containing, in addition to fats (40-47%) and proteins (15%) [Duke, J. D. Handbook of Energy Crops http://www.hort.purdue.edu/newcrop)], a series of diterpenoid esters known as $L_1$-$L_9$ *Euphorbia* Factors comprising a small but relatively constant amount of ingenol monoesters ($L_4$, $L_5$ and $L_6$) [Adolf W and Hecker E Z. Krebsforsch. 1975, 84, 325-344], the fraction containing ingenol being minor compared to the fraction containing the other types of diterpenoids. Ingenol esters are highly toxic, constituting a highly irritating oil, and even though ingenol alone isolated in free form is inoffensive, isolating ingenol from said esters is technically complex and not free of risk for the health of the operators involved in said isolation operations due to the aforementioned toxicity of the ingenol ester fraction.

A method for isolating ingenol from *E. lathyris* seeds was published in 1991 [Bagavathi R. et al., Naturforsch. 1991; 46b: 1425-1433]. Said method consisted of separating the fraction containing ingenol esters by means of a series of extractions with solvents, such as methanol, petroleum ether and chloroform, followed by selective adsorption in silica gels. The fraction containing ingenol esters was then subjected to hydrolysis and the ingenol obtained was finally purified by means of column chromatography techniques. Said method of isolating ingenol required a great deal of time and work due to the large number of steps or phases, its yield therefore being low and thereby complicating the development of new semi-synthetic derivatives that could potentially be used as drugs.

To solve the problem of the low efficiency and low yield of the method previously described in the state of the art for isolating ingenol, Appendino et al. [Appendino G et al., J Nat Prod. 1999; 62(1):76-9] developed a shorter and less toxic protocol for extracting and isolating ingenol because the time in contact with the irritating oil extracted from *E. lathyris* seeds containing ingenol esters and also containing macrocyclic diterpenoid compounds was less than that previously descried. In said method, isolating ingenol from *E. lathyris* seed oil was carried out in three basic steps. Briefly, (1) separating a crude diterpenoid fraction, (2) hydrolyzing the $L_1$-$L_9$ *Euphorbia* factors, and (3) separating ingenol from the polyols resulting from hydrolyzing macrocyclic diterpenoid esters (latirol, epoxylatirol, 7-hydroxylatirol, isolatirol, jolkinol, etc.). Both separations involve purifying a small concentration of ingenol from a complex mixture of natural compounds which have a similar polarity, which translates into obtaining an ingenol which, due to the complexity of the sample in which it is included and due to said similarity in the polarity of the compounds forming the aforementioned sample, can have impurities as it is contaminated with other substances present in the mentioned mixture, primarily non-hydrolyzed ingenol esters or esters of other macrocyclic diterpenoids.

The technical problem solved by the present invention is a method that is an alternative to those described in the state of the art of isolating ingenol from mixtures of diterpenoid esters and ingenol esters. These mixtures can have any origin, i.e., they can be natural (from plants) or generated in a chemical synthesis process. The invention preferably isolates ingenol from plants of the *Euphorbia* genus, and more specifically from *E. lathyris* seeds.

To solve the described problems existing in the state of the art for isolating ingenol, the present invention describes a method of isolating said compound from mixtures of diterpenoid esters and ingenol esters, preferably produced when processing *E. lathyris* seeds, with a higher yield than those known in the state of the art by simplifying the number of steps necessary for said isolation, reducing it to a single step (with an optional step of purification) and obtaining an ingenol with fewer impurities (purity >99%).

DESCRIPTION OF THE INVENTION

Brief Description of the Invention

The method described in the present invention combines hydrolyzing ingenol present in the mixture of diterpenoid esters and ingenol esters and separating said ingenol from said mixture in a single step. To that end, said mixture of diterpenoid esters and ingenol esters is treated with a solution of an organic solvent, preferably tetrahydrofuran (THF), and acidified water, more preferably acidified brine (water+salt). The method described in the present invention prevents isolating toxic or irritating intermediates, such as the ingenol ester fraction, simplifies the process and times for purifying ingenol and furthermore, the production yield of said compound is much greater than those known until now in the state of the art. Ingenol with a lower concentration of impurities is further obtained, which makes the ingenol thus isolated more suitable for being the starting compound in processes for obtaining derivatives thereof, with a higher yield and purity that can be used as drugs.

Ingenol obtained by means of the method described in the present invention can be used for obtaining esterified derivatives of said ingenol which are biologically active, such as ingenol-3-tigliate (Formula II) and ingenol-3-angelate (Formula ID) for example. The method of obtaining said biologically active derivatives includes an intermediate step of synthesizing the compound ingenol-5,20-acetonide (Formula IV) and subsequently its esterification (Diagram 1), to yield the aforementioned biologically active compounds according to techniques known in the state of the art for said purpose.

Diagram 1. Method of obtaining biologically active ingenol derivatives by means of methods known in the state of the art from ingenol obtained according to the method described in the present invention.

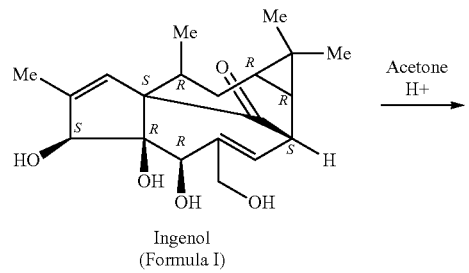

Ingenol
(Formula I)

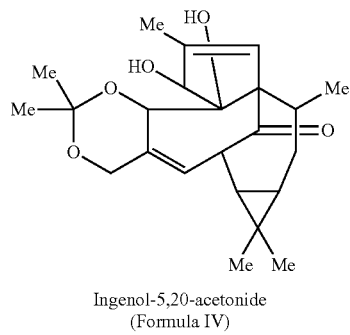

Ingenol-5,20-acetonide
(Formula IV)

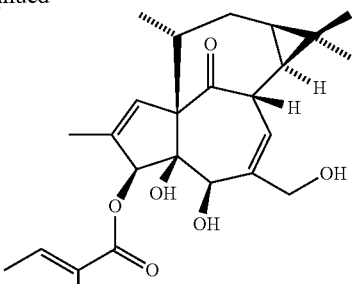

Ingenol-3-tigliate
(Formula II)

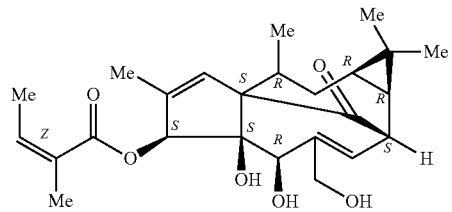

Ingenol-3-angelate
(Formula III)

The biologically active derivatives obtained from ingenol by means of the method described in the present invention presented purity greater than 99%. For the particular case of obtaining ingenol-3-angelate from ingenol obtained by means of the method described in the present invention, the production yield thereof significantly improves the yield of raw material per kg and is much more efficient and industrially scalable than the methods described in the state of the art for obtaining said product (Hohmann, J. et al., Planta Med. 2000, 66: 291-294). Therefore, the production yield of ingenol-3-angelate from *Euphorbia peplus* known in the state of the art is 1.1 mg per kg of plant, whereas with the method of the present invention, by combining the extraction of ingenol from *Euphorbia Lathyris* seed powder followed by a process for the partial chemical synthesis of the ingenol-3-angelate derivative, up to 190 mg per kg of *Euphorbia Lathyris* seed powder can be obtained.

DETAILED DESCRIPTION OF THE INVENTION

The object of the present invention relates to a method of isolating ingenol from mixtures comprising diterpenoid esters (including ingenol esters) combining the phases of hydrolyzing and isolating/extracting said ingenol in a single step and optionally further comprising an additional phase of purifying isolated ingenol. The terms isolating and extracting in relation to ingenol must be interpreted as being equivalents throughout the present invention.

To that end, the method of the invention subjects the mixture of diterpenoid esters and ingenol esters to a single step of combined treatment with an acidified water and organic solvent solution, preferably the ratio of acidified water to organic solvent is 1:1.

The preferred organic solvent is THF, and the acidified water also preferably contains inorganic salts, more preferably, the acidified water is an acidified brine containing NaCl. The concentration of NaCl present in the acidified water or brine is to saturation, i.e., approximately 35% weight/volume. For the purpose of the present invention, the term acidic brine refers to acidified water in which a specific concentration of inorganic salt or salts, specifically NaCl, is present.

In a preferred embodiment, the acidified water and organic solvent solution used in the method of the invention consists of a combination of $H_2SO_4$ at a concentration of 2N and $H_2O$+NaCl at 35% weight/volume (w/v), at a ratio of 1:1.

Optionally, the method of the invention further comprises an additional phase of purifying isolated ingenol. Said phase of purifying ingenol is preferably performed by means of gravity column chromatography.

In a preferred manner of carrying out the method of the invention, the single step of hydrolyzing and isolating/extracting ingenol is carried out in a process starting from plant material and comprising the phases of:

a) Subjecting the plant material, preferably 100 g of ground and homogenized seeds, to mechanical stirring for preferably 4 hours at room temperature in a methanol solution containing sodium methylate, preferably at a concentration of 0.20 N.

b) Neutralizing the preceding reaction with a solution of a glacial acetic acid or perchloric acid at a concentration of 0.03 M.

c) Filtering or suctioning the preceding solution preferably through celite.

d) Washing the pellet obtained in the previous phase with 70% methanol.

e) Concentrating the pellet preferably in a rotavapor.

f) Extracting from the previous pellet the fraction containing ingenol esters with petroleum ether.

g) Isolating ingenol from the remaining compounds comprised in the fraction obtained in the preceding phase f) by means of combined treatment with acidified water and THF in a single step.

h) Optionally purifying the ingenol isolated in the preceding phase.

In a preferred embodiment of the invention the plant material is *Euphorbia lathyris* seeds.

The mechanical stirring is preferably carried out by means of a rotor driven by an electric motor. In a preferred embodiment of the invention, the seeds are subjected to this mechanical stirring after having been previously ground, and more preferably ground to seed powder.

In another preferred embodiment of the method of isolating ingenol from a starting plant material used, the acidified water solution preferably consists of a combination of $H_2SO_4$ at a concentration of 2N and $H_2O+NaCl$ at 35% w/v at a ratio of 1:1.

In another preferred embodiment of the method of isolating ingenol from a starting plant material used, the phase of purifying ingenol is performed by means of gravity column chromatography, preferably using a silica gel column as stationary phase with a petroleum ether-ethyl acetate mobile phase.

As repeatedly mentioned, ingenol produced by means of the method of the invention can be used as a precursor for obtaining biologically active derivatives thereof, preferably for obtaining ingenol-3-tigliate (Formula II) and ingenol-3-angelate (Formula III), which can be used in clinical practice for the treatment of different pathologies. Said derivatives as well as the ingenol itself isolated according to the method of the invention, are obtained with degrees of purity >99%.

To that end, in a preferred embodiment of the invention, the optionally purified isolated ingenol, whether it is obtained from a mixture of ingenol esters and diterpenoid esters of any origin or said mixture is generated from a plant material source, preferably $E.$ $lathyris$ seeds, said ingenol is subjected to an additional process of partial chemical synthesis to produce a derivative at position 3 selected from: ingenol-3-tigliate (Formula II), ingenol-3-angelate (Formula III), or mixtures thereof. Preferably, said additional process of partial chemical synthesis for obtaining ingenol derivatives at position 3 to which the optionally purified isolated ingenol is subjected has ingenol-5,20-acetonide as the common intermediate compound (Formula IV).

The object of the examples described below is to illustrate the invention without limiting the scope thereof.

EXAMPLE 1

Method of Isolating Ingenol (Formula 1) from
*Euphorbia lathyris* L (Spurge) Seeds The *Euphobia lathyris* L seed powder (1 kg) was mechanically stirred in a solution of 2 l of sodium methylate in 0.20 N methanol for 4 hours. After said time, the solution was neutralized with glacial acetic acid (or perchloric acid) and filtered and/or suctioned through a bed of celite. The pasta obtained of said filtration was washed several times with methanol (100 ml every time), and the filtered materials were concentrated by means of vacuum techniques to a volume of 1.5 l and were subsequently extracted with petroleum ether. The methanol phase obtained from said extraction was evaporated with a rotary evaporator and the resulting residue was subjected to solution of acidic brine (2N $H_2SO_4$+brine 1:1, 0.5 l) and THF (0.2 l), at room temperature. The upper phase obtained was evaporated at 80° C., and the residue was purified by gravity silica gel column chromatography (150 ml) using a petroleum ether-EtOAc (ethyl acetate) gradient until obtaining 0.750 g of ingenol (Formula 1) with a purity >99%.

EXAMPLE 2

Producing Ingenol-5,20-acetonide (Formula IV)

Pyridinium p-toluenesulfonate (50 mg) was added to a solution of ingenol (100 mg, 0.29 mmol) dissolved in acetone (5 ml). The solution was stirred at room temperature for 12 hours and was then subjected to evaporation. The residue was purified by gravity column chromatography until reaching 62 mg (55% yield) of ingenol-5,20-acetonide (Formula IV). For physical and spectroscopic data, see Bangavathi R. et al. On the Chemistry of Ingenol IV. Z. Naturforsch. 1991, 46b, 1425-1433.

EXAMPLE 3

Producing Ingenol Tigliate (Formula II)

A solution of ingenol-5,20-acetonide (100 mg, 0.26 mmol), tiglic acid (39 mg, 0.39 mmol, 1.5 mol. equiv.) and DMAP (48 mg, 0.39 mmol, 1.5 mol. equiv.) in toluene (4 ml), was stirred at room temperature for 2 hours and was then filtered through a bed of Celite and evaporated. The resulting material was filtered in silica gel (about 5 g) and evaporated. The residue was purified by means of silica gel gravity column chromatography (5 g, petroleum ether:EtOAc 85:15) until obtaining over 80 mg of ingenol-3-tigliate with a purity>99%). For physical and spectroscopic data, see Hohmann J et al. Planta Medica 2000, 66, 291-294.

EXAMPLE 4

Producing Ingenol Angelate (Formula III)

A solution of ingenol-5,20-acetonide (100 mg, 0.26 mmol), angelic acid (39 mg, 0.39 mmol, 1.5 mol. equiv.) and DMAP (48 mg, 0.39 mmol, 1.5 mol. equiv.) in toluene (4 ml), was stirred at room temperature for 2 hours and was then filtered through a bed of celite and evaporated. The resulting material was filtered in silica gel (ca. 5 g) and evaporated. The residue was purified by means of silica gel gravity column chromatography (5 g, petroleum ether:EtOAc 85:15) until obtaining over 80 mg of ingenol-3-angelate with a purity>99%. For physical and spectroscopic data, see Hohmann J et al. Planta Medica 2000, 66, 291-294.

LITERATURE

Adolf W and Hecker E Z. Krebsforsch. 1975, 84, 325-344.
Appendino G et al., An expeditious procedure for the isolation of Ingenol from the *Euphorbia lathyris* seeds. J Nat Prod. 1999 January; 62(1):76-9.
Bangavathi R. et al. On the Chemistry of Ingenol IV. Z. Naturforsch. 1991, 46b, 14251433.
Benhadji K A et al. Antiproliferative activity of PEP005, a novel ingenol angelate that modulates PKC functions, alone and in combination with cytotoxic agents in human colon cancer cells. Br J Cancer. 2008 Dec. 2; 99(11):1808-15.
Duke, J. D. Handbook of Energy Crops (Available on the Internet at http://www.hort.purdue.edu/newcrop).
Evans F J and Kinghorn A D J. Linn. Soco Bot. (London) 1977, 74, 23-35.
Evans, F. J. and Taylor, S. E., in *Progress in the Chemistry of Organic Natural Products*, Vol. 44, ed. W. Herz, H. Grisebach and G. W. Kirby. Springer, Vienna, 1983, p. I.
Fujiwara M et al., Mechanism of selective inhibition of human immunodeficiency virus by ingenol triacetate. Antimicrob Agents Chemother. 1996 January; 40(1): 271-3.
Herz W, Fujiwara M et al. Upregulation of HIV-1 replication in chronically infected cells by ingenol derivatives. Arch Virol. 1998; 143(10):2003-10.

Hohmann, J. et al. Diterpenoids from *Euphorbia peplus*. Planta Med. 66 (2000); 291: 294.

Kedei N et al. Characterization of the interaction of ingenol-3-angelate with protein kinase C. Cancer Res. 2004; 64(9):3243-55.

Le T I et al. Immunostimulatory cancer chemotherapy using local ingenol-3-angelate and synergy with immunotherapies. Vaccine. 2009 May 18; 27(23):3053-62.

Mainieri F et al. Synthesis of Sapintoxin D and N-Methylanthranilate-based Fluorescent Bioprobes. Nat. Prod. Commun. 2007, 2, 375-379.

Ogbourne S M et al. Antitumor activity of 3-ingenyl angelate: plasma membrane and mitochondrial disruption and necrotic cell death. Cancer Res 2004; 64:2833-9.

Olsnes A M et al. The protein kinase C agonist PEP005 increases NF-kappaB expression, induces differentiation and increases constitutive chemokine release by primary acute myeloid leukaemia cells. Br J Haematol. 2009 June; 145(6):761-74.

Warrilow D et al., HIV type 1 inhibition by protein kinase C modulatory compounds. AIDS Res Hum Retroviruses. 2006 September; 22(9):854-64.

The invention claimed is:

1. A method of isolating ingenol from plant material, said method comprising:
   a) subjecting said plant material to mechanical stirring in a solution of sodium methylate in methanol to obtain a solution containing hydrolyzed ingenol;
   b) extracting from the preceding solution a fraction containing ingenol with an acidified water consisting of a glacial acetic acid or perchloric acid at a concentration of 0.03 M and an organic solvent solution to obtain a fraction containing ingenol; and
   c) optionally purifying the ingenol to provide an isolated ingenol, wherein said plant material are *Euphorbia lathyris* seeds.

2. The method according to claim 1, wherein the concentration of sodium methylate in methanol is 0.20 N and the time for which the seeds are subjected to mechanical stirring is 4 hours.

3. The method according to claim 1, further comprising filtering or suctioning on celite the solution obtained in step a).

4. The method according to claim 1 wherein the step of purifying ingenol is performed by means of gravity column chromatography.

5. The method according to claim 4, wherein a silica gel column is used as a stationary phase with a petroleum ether-ethyl acetate as a mobile phase.

6. The method according to claim 1, wherein the purified isolated ingenol is subjected to an additional process of partial chemical synthesis to produce a derivative at position 3 selected from: ingenol-3-tigliate, ingenol-3-angelate or mixtures thereof.

7. The method according to claim 6, wherein the additional process of partial chemical synthesis for obtaining ingenol derivatives at position 3 to which the purified isolated ingenol is subjected has ingenol-5,20-acetonide as the common intermediate.

* * * * *